(12) United States Patent
Tindal et al.

(10) Patent No.: US 8,709,098 B2
(45) Date of Patent: Apr. 29, 2014

(54) DEPILATORY COMPOSITION

(75) Inventors: Anne Tindal, Hull (GB); Oumou Mangassi, Hull (GB)

(73) Assignee: Reckitt & Colman (Overseas) Limited, Slough, Berkshire (GB)

( * ) Notice: Subject to any disclaimer, the term of this patent is extended or adjusted under 35 U.S.C. 154(b) by 0 days.

(21) Appl. No.: 12/530,426

(22) PCT Filed: Mar. 3, 2008

(86) PCT No.: PCT/GB2008/000731
§ 371 (c)(1),
(2), (4) Date: Oct. 30, 2009

(87) PCT Pub. No.: WO2008/110745
PCT Pub. Date: Sep. 18, 2008

(65) Prior Publication Data
US 2010/0083443 A1    Apr. 8, 2010

(30) Foreign Application Priority Data
Mar. 9, 2007 (GB) .................................. 0704599.0

(51) Int. Cl.
*C14C 1/06* (2006.01)

(52) U.S. Cl.
USPC .................................................. 8/94.16

(58) Field of Classification Search
USPC .................................................... 8/94.16
See application file for complete search history.

(56) References Cited

U.S. PATENT DOCUMENTS

| 4,631,064 A * | 12/1986 | Juneja .................. 8/161 |
| 5,378,455 A * | 1/1995 | Kealey et al. .................. 424/73 |
| 5,725,847 A | 3/1998 | De La Mettrie et al. |
| 6,126,953 A * | 10/2000 | Costa et al. .................. 424/401 |
| 6,479,043 B1 | 11/2002 | Tietjen et al. |
| 2002/0086039 A1* | 7/2002 | Lee et al. .................. 424/401 |
| 2002/0146380 A1 | 10/2002 | Nambu et al. |
| 2004/0180014 A1 | 9/2004 | Gupta |
| 2005/0265948 A1* | 12/2005 | Ridley et al. .................. 424/70.16 |
| 2006/0104966 A1* | 5/2006 | Green et al. .................. 424/94.5 |
| 2007/0020220 A1* | 1/2007 | Osborne .................. 424/70.14 |
| 2007/0031361 A1* | 2/2007 | Herrmann et al. .......... 424/70.11 |
| 2007/0219158 A1* | 9/2007 | Aoki et al. .................. 514/54 |

FOREIGN PATENT DOCUMENTS

| EP | 0307129 A | 3/1989 | |
| EP | 1902752 A | 3/2008 | |
| FR | 2883169 A1 * | 9/2006 | ............... A61K 8/04 |
| WO | WO2005/123022 A | 12/2005 | |
| WO | WO2007/031793 A | 3/2007 | |

OTHER PUBLICATIONS

Combined Search and Examination Report of GB 0704599.0, dated Jun. 28, 2007.
International Search Report of PCT/GB2008/000731, dated Nov. 6, 2008.

* cited by examiner

*Primary Examiner* — Harold Pyon
*Assistant Examiner* — Tanisha Diggs
(74) *Attorney, Agent, or Firm* — Troutman Sanders LLP; Ryan A. Schneider

(57) ABSTRACT

A depilatory cream composition comprising, a depilatory active, an emollient selected from at least one of mineral oil, silicone oil and emollient esters, and a silicone wax, a talc and/or polyamide resin.

14 Claims, No Drawings

DEPILATORY COMPOSITION

BENEFIT CLAIMS

This application is a US National Stage of International Application No. PCT/GB2008/000731, filed 3 Mar. 2008, which claims the benefit of GB 0704599.0, filed 9 Mar. 2007.

FIELD OF THE INVENTION

The present invention relates to a depilatory cream composition and its method of use. The present invention also relates to the use of silicone wax, polyamide resin and/or a mineral to improve the skin-feel of a depilatory cream composition.

BACKGROUND OF THE INVENTION

Depilatory creams for removing unwanted hair are known. Such creams typically include a depilatory active that degrades hair keratin.

BRIEF SUMMARY OF THE INVENTION

A depilatory cream with an improved skin-feel has now been developed.

According to a first aspect of the present invention there is provided a depilatory cream composition comprising
  a depilatory active,
  an emollient selected from at least one of mineral oil, silicone oil and emollient esters, and
  a silicone wax, a talc and/or a polyamide resin.

According to a second aspect of the present invention, there is provided the use of silicone wax, polyamide resin and/or talc to improve the skin-feel of a depilatory cream composition.

According to a third aspect of the present invention, there is provided a method of depilation comprising:
  a. applying a composition as defined above to the skin;
  b. allowing the composition a residence time on the skin in order to degrade hairs on the skin's surface;
  c. at the end of the residence time removing the composition and depilated hairs form the skin; and
  d. rinsing the skin.

DETAILED DESCRIPTION OF PREFERRED EMBODIMENTS

It has been found that, by incorporating a skin-feel enhancing agent selected from at least one of silicone wax, talc and polyamide resin in the depilatory cream composition, the skin-feel of the composition is improved. In particular, the silicone wax, talc and/or a polyamide resin impart(s) a soft and velvety after-feel to the depilatory cream composition without affecting the composition's hair removal properties.

Talc is particularly preferred over other minerals which have previously been used in cosmetics as it confers a powdery after-feel which is desirable. In addition, it does not alter the colour of the composition.

The depilatory cream composition may further include a humectant. Suitable humectants include polyols, such as glycerine, propylene glycol and butylene glycol. Glycerine is preferred. The humectant may be present in an amount of 0 to 10 weight %, preferably 0.5 to 5 weight %.

Preferably, the composition comprises talc.

The talc may be present in an amount of 0.1 to 10 weight %, preferably 0.2 to 5 weight %, more preferably 0.5 to 3 weight %. In one embodiment, the composition includes 1 to 2 weight % talc.

The composition may comprise a polyamide resin as an alternative or in addition to the mineral. The polyamide resin is preferably Nylon-12.

The polyamide resin, preferably Nylon-12, may be present in an amount of 0.1 to 10 weight %, preferably 0.5 to 5 weight %, more preferably 1 to 3 weight %, for example 2 weight %.

The composition may also comprise a silicone wax as an alternative or in addition to the mineral and/or polyamide resin. Suitable silicone waxes include $C_{30}$-$C_{45}$ alkyl methicone and a silicone wax formed from stearoxytrimethylsilane and stearyl alcohol. The silicone wax is preferably $C_{30}$-$C_{45}$ alkyl methicone.

Where a silicone wax is employed, the composition preferably includes a silicone oil to optimise the skin-feel properties of the composition. Preferably a silicone oil selected from dimethicone, cyclopentasiloxane and dimethiconol. In a preferred embodiment, the composition includes dimethicone, cyclopentasiloxane and dimethiconol in combination with a silicone wax (preferably $C_{30}$-$C_{45}$ alkyl methicone)

The silicone wax may be present in an amount of 0.1 to 10 weight %, preferably 0.5 to 5 weight %, more preferably 1 to 3 weight %, for example 1 to 2 weight %.

The emollient is selected from at least one of mineral oil, silicone and emollient esters. Together with the silicone wax, mineral and/or polyamide resin (and optional humectant), the emollient plays an important role in providing the depilatory cream composition with its desired skin-feel characteristics.

The emollient may be present in an amount of 1 to 10 weight %, preferably 3 to 7 weight % of the composition.

Mineral oil may be present in an amount of 0 to 10 weight %, preferably 0.5 to 5 weight % of the composition.

Silicone oil may be present in an amount of 0 to 10 weight %, preferably 0.5 to 5 weight %, for example 1 to 4 weight % of the composition.

Emollient esters may be present in an amount of 0 to 10 weight %, preferably 0.5 to 5 weight % of the composition, for example 1 to 3 weight %.

It is possible for the emollient to consist essentially of mineral oil. For example, in one embodiment, the composition includes talc and an emollient that consists essentially of mineral oil. In this embodiment, the emollient is present in an amount of 3 to 6 weight %, preferably 5 weight %. The talc is present in an amount of 0.3 to 1 weight %, preferably 0.5 weight %. Where an emollient consisting essentially of mineral oil emollient is employed, the composition preferably includes a humectant, such as glycerine.

It is also possible for the emollient to comprise or consist essentially of silicone oil(s). Preferably, a combination of silicone oils are present. The silicone oil may include at least one of cyclopentasiloxane, dimethiconol and dimethicone. Preferably, the silicone oil comprises cyclopentasiloxane, dimethiconol and dimethicone. The silicone oil may include 0.1 to 5 weight %, preferably 1 to 2 weight % dimethicone; and/or 1 to 5 weight %, for example, 1 to 3 weight % cyclopentasiloxane and dimethiconol.

It is possible for the emollient to consist essentially of an emollient ester. However, the emollient ester is preferably used in combination with a mineral oil and/or a silicone oil.

In one embodiment, the emollient comprises at least two of mineral oil, silicone oil and emollient esters. For example, the emollient may include mineral oil and silicone oil, or mineral oil and emollient esters, or silicone oil and emollient esters. In one embodiment, the emollient includes mineral oil, silicone oil and emollient esters.

Any suitable silicone oil may be employed. Examples include cyclopentasiloxane, dimethiconol and dimethicone. In one embodiment, the silicone oil comprises cyclopentasiloxane and dimethiconol. In another embodiment, the silicone oil comprises dimethicone, cyclopentasiloxane and dimethiconol. The total amount of silicone oil in the composition may be 0.1 to 10 weight %, for example, 2 to 5 weight %. Where dimethicone is employed, the amount of dimethicone may range from 0.1 to 5 weight %, for example 1 to 2 weight %. Where cyclopentasiloxane and dimethiconol are employed, this combination may be present in an amount of 0.1 to 5 weight %, for example 1 to 3 weight %.

Any suitable emollient ester may be employed. Suitable examples include isopropyl palmitate, isopropyl myristate, myristyl lactate, cetyl esters, isotridecyl isononanoate, $C_{12-15}$ alkyl benzoate, caprylic/capric triglyceride and pentaerythrityl tetraisostearate.

In one embodiment, the emollient comprises mineral oil, pentaerythrityl tetraisostearate, cyclopentasiloxane and dimethiconol. The mineral oil may be present in an amount of 3 to 6 weight %, preferably 5 weight %. The pentaerythrityl tetraisostearate may be present in an amount of 1 to 3 weight %, preferably 1 weight %. The cyclopentasiloxane and dimethiconol may be present in an amount of 1 to 3 weight %, preferably 1 weight %. In a preferred embodiment, this combination of emollients is used together with at least one of talc and polyamide resin.

The depilatory active is a compound capable of degrading keratin and may be, for example, a sulphur compound such as potassium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptropropionic acid, thiomalic acid, ammonium thioglycolate, glyceryl monothioglycolate, monoethanolamine thioglycolate, monoethanolamine, thioglycolic acid, diammonium dithiodiglycolate, ammonium thiolactate, monoethanolamine thiolactate, thioglycolamide, homo-cysteine, cysteine, glutathione, dithiothreitol, dihydrolipoic acid, 1,3-dithiopropanol, thioglycolamide, glycerylmonothioglycolate, thioglycolhydrazine, keratinase, hydrazine sulphate, hydrazine disulphate triisocyanate, guanidine thioglycolate, calcium thioglycolate and/or cysteamine. However, the composition is preferably substantially or, more preferably, is completely free from depilatory agents that destroy the thermodynamic equilibrium or the surface tension of the composition; examples of such agents include alkali metal sulphides.

Preferred depilatory compounds are thioglycolates, or their precursor thioglycolic acid. Most preferred is potassium thioglycolate, which may be produced by mixing thioglycolic acid with a neutralising source of potassium hydroxide (as noted above excess potassium hydroxide over that required to effect neutralisation cannot be used).

The depilatory active may be present in an amount of 2 to 25 weight %, preferably 5 to 20 weight %, more preferably 10 to 15 weight %. In one embodiment, the composition includes potassium thioglycolate in an amount of 2 to 25 weight %, preferably 5 to 20 weight %, more preferably 10 to 15 weight %.

The depilatory cream composition of the present invention preferably includes water. Water may be present in an amount of at least 40 weight %, preferably at least 50 weight %. Suitable amounts of water range from 40 to 70 weight %, preferably 50 to 65 weight %, more preferably 55 to 60 weight %.

The depilatory cream composition may include an oil. Suitable oils include sweet almond oil, iso-hexane, sunflower seed oil, apricot kernel oil and/or shea butter. Preferably, sweet almond oil is employed. The oil may form 0.01 to 5 weight %, more preferably 0.1 to 1 weight %, of the depilatory cream composition.

The depilatory cream composition may optionally include one or more surfactant(s). The surfactant may be anionic, cationic or non-ionic. It is preferably non-ionic. Examples of suitable surfactants include cetearyl phosphate, cetearyl alcohol, cetearyl glucoside, cetostearyl alcohol and/or ceteareth 20. It is preferably present in an amount of from 0.5 to 15 wt % relative to the weight of the depilatory cream composition, more preferably from 1 to 10 wt %.

The depilatory cream composition may optionally include a source of alkalinity. This may include hydroxides, such as hydroxides of alkali and alkaline earth metals. Suitable hydroxides include sodium hydroxide, potassium hydroxide, calcium hydroxide and magnesium hydroxide. Preferably, calcium hydroxide is employed, optionally together with potassium hydroxide. The source of alkalinity (e.g. calcium hydroxide) may be present in an amount of 0.1 to 10 weight %, preferably 1 to 6 weight %, for example 2 to 5 weight % of the depilatory cream composition.

The depilatory cream composition preferably has a pH of greater than 7, for example, 9 to 12.5.

Optionally, the composition includes an accelerator that will accelerate the hair removal reaction. Examples of such accelerators include urea, thiourea, dimethyl, isosorbide (DMI), ethoxydiglycol (Transcutol) or methyl propyl diol (MP diol). Preferably the accelerator is urea. The composition according to the invention preferably comprises from 5% to 15% wt, more preferably from 6 to 10 wt % of an accelerator (e.g. urea).

The depilatory cream composition may comprise other optional ingredients, such as perfumes, pigments and fillers, such as clays. Examples of suitable clays include sodium magnesium silicate, magnesium trisilicate and titanium dioxide. The inclusion of a clay, preferably sodium magnesium silicate, more preferably in an amount of from 0.1 to 10 wt % relative to the weight of the depilatory composition, most preferably from 0.1 to 1 wt %, is particularly advantageous, since this provides sodium and magnesium ions for the buffer system and improves the efficiency of depilation.

The depilatory cream composition desirably includes a chelating agent, such as sodium gluconate. The chelating agent may be present in an amount of less than 1 weight %, preferably 0.01 to 0.5 weight %, for example 0.05 to 0.1 weight %.

The depilatory cream composition may also include an additive that prevents phase separation. Suitable additives include polymers or copolymers of acrylic acid, for example, an acrylate copolymer. Such additives may be present in an amount of up to 2 weight %, preferably less than 1 weight %, more preferably less than 0.5 weight %, for example 0.1 to 0.4 weight %.

The depilatory cream composition may also include an malodour absorbent, such as spray dried silica. Such absorbents may be present in an amount of up to 2 weight %, preferably less than 1 weight %, more preferably less than 0.5 weight %, for example 0.001 to 0.1 weight %.

Optionally, additives such as aloe vera and Vitamin E may also be included in the composition. Such additives are employed in amounts of less than 1 weight %, for example, 0.1 to 0.5 weight % of the composition.

The depilatory cream composition may be made by first mixing components, such as the emollient and silicone wax, polyamide resin and/or talc, together to form a pre-mix. The pre-mix may be made at a temperature not exceeding 85° C., preferably in the range 65° C. to 80° C. The pre-mix may be actively or passively cooled. The depilatory compound may then be mixed with the pre-mix. The resulting mixture may be mixed at a temperature in the range 15° C. to 40° C.

In the method of depilation of the present invention the composition is allowed a residence time on the skin. Preferably the residence time is less than 10 minutes, more preferably not more than 6 minutes, even. Very suitably the residence time is 1 to 5 minutes, about 2 to 3 minutes being especially preferred.

It is found that using the composition of the present invention depilation after a residence time of only 3 minutes can be excellent, yet without significant skin irritation in subjects with normal skin.

The composition may be removed from the skin by any means, for example using a sponge, spatula or scraper device.

An advantage of the composition of the present invention is that it leaves the skin feeling soft and smooth. The composition of the present invention preferably also feels smooth and soft when applied to the skin.

The following Examples further illustrate the present invention.

Example 1

| Component | Weight % |
| --- | --- |
| Deionised Water$^a$ | 38.245 |
| Cetearyl alcohol 30/70$^a$ | 3.9 |
| Ceteareth-20$^a$ | 1.76 |
| Paraffinum Liquidum$^a$ | 4.5 |
| Sweet Almond oil$^a$ | 0.1 |
| Pentaerythrityl Tetraisostearate$^a$ | 0.8 |
| Cyclopentasiloxane and Dimethiconol$^a$ | 1.2 |
| Calcium hydroxide$^a$ | 3.56 |
| Sodium gluconate$^a$ | 0.1 |
| Nylon 12$^a$ | 2 |
| Magnesium trisilicate$^a$ | 0.5 |
| PMX, Depil, white paste$^a$ | 0.6 |
| Deionised water$^b$ | 20.5 |
| Urea$^b$ | 8.0 |
| Na Mg silicate$^b$ | 0.2 |
| Acrylates copolymer 33$^b$ | 0.1 |
| Aloe vera$^b$ | 0.1 |
| Potassium thioglycolate | 12.25 |
| Potassium hydroxide (50%) | 1 |
| Fragrance$^c$ | 0.56 |
| Spray dried silica$^c$ | 0.025 |

The ingredients labelled "a" were mixed together at a temperature of approximately 70 degrees C. The mixture was then cooled and a pre-mix containing ingredients "b" was added at a temperature of approximately 50 degrees C. The resulting mixture was agitated further and then cooled. A pre-mix of ingredients "c" was then added at a temperature of approximately 40 degrees C., together with the potassium thioglycolate and potassium hydroxide.

Example 2

| Component | Weight % |
| --- | --- |
| Deionised Water$^a$ | 36.245 |
| Cetearyl alcohol 30/70$^a$ | 4.9 |
| Ceteareth-20$^a$ | 2.26 |
| Paraffinum liquidum$^a$ | 5 |
| Sweet almond oil$^a$ | 0.1 |
| Pentaerythrityl Tetraisostearate$^a$ | 1.2 |
| Cyclopentasiloxane and Dimethiconol$^a$ | 0.8 |
| Calcium hydroxide$^a$ | 3.56 |
| Sodium gluconate$^a$ | 0.1 |
| Talc$^a$ | 2 |
| Magnesium trisilicate$^a$ | 0.5 |
| PMX, Depil, white paste$^a$ | 0.6 |
| Deionised water$^b$ | 20.5 |
| Urea$^b$ | 8.0 |
| Na Mg silicate$^b$ | 0.2 |
| Acrylates copolymer 33$^b$ | 0.1 |
| Aloe vera$^b$ | 0.1 |
| Potassium thioglycolate | 12.25 |
| Potassium hydroxide (50%) | 1 |
| Fragrance$^c$ | 0.56 |
| Spray dried silica$^c$ | 0.025 |

The ingredients labelled "a" were mixed together at a temperature of approximately 70 degrees C. The mixture was then cooled and a pre-mix containing ingredients "b" was added at a temperature of approximately 50 degrees C. The resulting mixture was agitated further and then cooled. A pre-mix of ingredients "c" was then added at a temperature of approximately 40 degrees C., together with the potassium thioglycolate and potassium hydroxide.

Example 3

| Component | Weight % |
| --- | --- |
| Deionised Water$^a$ | 36.205 |
| Cetearyl alcohol 30/70$^a$ | 5.5 |
| Ceteareth-20$^a$ | 2.7 |
| Paraffinum liquidum$^a$ | 5.5 |
| Sweet almond oil$^a$ | 0.1 |
| Glycerin$^a$ | 2 |
| Calcium hydroxide$^a$ | 3.56 |
| Sodium gluconate$^a$ | 0.15 |
| Talc$^a$ | 0.45 |
| Magnesium trisilicate$^a$ | 0.5 |
| PMX, Depil, white paste$^a$ | 0.6 |
| Deionised water$^b$ | 20.5 |
| Urea$^b$ | 8.0 |
| Na Mg silicate$^b$ | 0.2 |
| Acrylates copolymer 33$^b$ | 0.1 |
| Aloe vera$^b$ | 0.1 |
| Potassium thioglycolate | 12.25 |
| Potassium hydroxide (50%) | 1 |
| Fragrance$^c$ | 0.56 |
| Spray dried silica$^c$ | 0.025 |

The ingredients labelled "a" were mixed together at a temperature of approximately 70 degrees C. The mixture was then cooled and a pre-mix containing ingredients "b" was added at a temperature of approximately 50 degrees C. The resulting mixture was agitated further and then cooled. A pre-mix of ingredients "c" was then added at a temperature of approximately 40 degrees C., together with the potassium thioglycolate and potassium hydroxide.

Example 4

| Component | Weight % |
|---|---|
| Deionised Water$^a$ | 41.245 |
| Cetearyl alcohol 30/70$^a$ | 4.4 |
| Ceteareth-20$^a$ | 1.76 |
| $C_{30}$ to $C_{45}$ alkyl methicone$^a$ | 0.75 |
| Cyclopentasiloxane and Dimethiconol$^a$ | 3.5 |
| Dimethicone$^a$ | 0.75 |
| Sweet almond oil$^a$ | 0.1 |
| Calcium hydroxide$^a$ | 3.56 |
| Sodium gluconate$^a$ | 0.1 |
| Magnesium trisilicate$^a$ | 0.5 |
| PMX, Depil, white paste$^a$ | 0.6 |
| Deionised water$^b$ | 20.5 |
| Urea$^b$ | 8.0 |
| Na Mg silicate$^b$ | 0.2 |
| Acrylates copolymer 33$^b$ | 0.1 |
| Aloe vera$^b$ | 0.1 |
| Potassium thioglycolate | 12.25 |
| Potassium hydroxide (50%) | 1 |
| Fragrance$^c$ | 0.56 |
| Spray dried silica$^c$ | 0.025 |

The ingredients labelled "a" were mixed together at a temperature of approximately 70 degrees C. The mixture was then cooled and a pre-mix containing ingredients "b" was added at a temperature of approximately 50 degrees C. The resulting mixture was agitated further and then cooled. A pre-mix of ingredients "c" was then added at a temperature of approximately 40 degrees C., together with the potassium thioglycolate and potassium hydroxide.

Example 5

| Component | Weight % |
|---|---|
| Deionised Water$^a$ | 37.245 |
| Cetearyl alcohol 30/70$^a$ | 4.4 |
| Ceteareth-20$^a$ | 1.76 |
| Paraffinum liquidum$^a$ | 6.5 |
| Sweet almond oil$^a$ | 0.1 |
| Calcium hydroxide$^a$ | 3.56 |
| Sodium gluconate$^a$ | 0.1 |
| Talc$^a$ | 2.5 |
| Magnesium trisilicate$^a$ | 0.75 |
| PMX, Depil, white paste$^a$ | 0.85 |
| Deionised water$^b$ | 20.5 |
| Urea$^b$ | 8.0 |
| Na Mg silicate$^b$ | 0.2 |
| Acrylates copolymer 33$^b$ | 0.1 |
| Aloe vera$^b$ | 0.1 |
| Potassium thioglycolate | 12.25 |
| Potassium hydroxide (50%) | 1 |
| Fragrance$^c$ | 0.56 |
| Spray dried silica$^c$ | 0.025 |

The ingredients labelled "a" were mixed together at a temperature of approximately 70 degrees C. The mixture was then cooled and a pre-mix containing ingredients "b" was added at a temperature of approximately 50 degrees C. The resulting mixture was agitated further and then cooled. A pre-mix of ingredients "c" was then added at a temperature of approximately 40 degrees C., together with the potassium thioglycolate and potassium hydroxide.

What is claimed is:

1. A depilatory cream composition consisting of:
   a depilatory active,
   an emollient consisting of a mineral oil, a silicone oil, and an emollient ester, wherein the emollient is present at a concentration greater than about 5 weight % to about 10 weight %, and
   a skin-feel enhancing agent.

2. A composition as claimed in claim 1, wherein the skin-feel enhancing agent is a polyamide resin.

3. A composition as claimed in claim 1, wherein the skin-feel enhancing agent is a silicone wax.

4. A composition as claimed in claim 2, wherein the polyamide resin is a Nylon-12 resin.

5. A composition as claimed in claim 3, wherein the silicone wax is $C_{30}$-$C_{45}$ alkyl methicone.

6. A composition as claimed in claim 1, wherein the silicone oil is selected from at least one of cyclopentasiloxane, dimethiconol and dimethicone.

7. A composition as claimed in claim 1, wherein the skin-feel enhancing agent consists of 5-10 weight % of talc and a silicone wax, and the silicone oil consists of dimethicone, cyclopentasiloxane and dimethiconol.

8. A composition as claimed in claim 1, wherein the emollient ester is pentaerythrityl tetraisostearate.

9. A composition as claimed in claim 1, which consists of 2 to 20 weight % depilatory active.

10. A composition as claimed in claim 1, wherein the emollient is present at a concentration of about 7 weight %.

11. A depilatory cream composition consisting of:
    a depilatory active,
    an emollient consisting of a mineral oil, a silicone oil and an emollient ester,
    a skin-feel enhancing agent consisting of 5-10 weight % of talc, and a humectant.

12. A composition as claimed in claim 11, wherein the humectant is glycerine.

13. A depilatory cream composition consisting of:
    a depilatory active,
    an emollient consisting of a mineral oil, a silicone oil and an emollient ester, wherein the emollient is present at a concentration greater than about 5 weight % to about 10 weight %, and
    a skin-feel enhancing agent consisting of 5-10 weight % of talc,
    wherein the silicone oil consists of cyclopentasiloxane and dimethiconol, and wherein the emollient ester is pentaerythrityl tetrastearate.

14. A method of depilation comprising:
    applying a composition as claimed in claim 1 to the skin;
    allowing the composition a residence time on the skin in order to degrade the hairs on the skin's surface;
    at the end of the residence time removing the composition and depilated hairs from the skin; and
    rinsing the skin.

* * * * *